US008098859B2

(12) United States Patent
Zeng et al.

(10) Patent No.: US 8,098,859 B2
(45) Date of Patent: Jan. 17, 2012

(54) METHODS, DEVICES AND SYSTEMS USING SIGNAL PROCESSING ALGORITHMS TO IMPROVE SPEECH INTELLIGIBILITY AND LISTENING COMFORT

(75) Inventors: Fan-Gang Zeng, Irvine, CA (US); Sheng Liu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 782 days.

(21) Appl. No.: 11/917,320

(22) PCT Filed: Jun. 8, 2006

(86) PCT No.: PCT/US2006/022606

§ 371 (c)(1), (2), (4) Date: Sep. 26, 2008

(87) PCT Pub. No.: WO2006/133431

PCT Pub. Date: Dec. 14, 2006

(65) Prior Publication Data

US 2009/0226015 A1 Sep. 10, 2009

Related U.S. Application Data

(60) Provisional application No. 60/688,918, filed on Jun. 8, 2005.

(51) Int. Cl.

*H04R 25/00* (2006.01)
*A61N 1/36* (2006.01)
*A61F 11/04* (2006.01)

(52) U.S. Cl. .......................................... 381/316; 607/57

(58) Field of Classification Search ................... 381/316

See application file for complete search history.

(56) References Cited

U.S. PATENT DOCUMENTS

| | | | |
|---|---|---|---|
| 6,577,739 | B1 | 6/2003 | Hurtig et al. |
| 2002/0037088 | A1 | 3/2002 | Dickel et al. |
| 2005/0197832 | A1 | 9/2005 | Vandali et al. |

*Primary Examiner* — Victor A Mandala
*Assistant Examiner* — Whitney T Moore
(74) *Attorney, Agent, or Firm* — Dickstein Shapiro LLP

(57) ABSTRACT

Methods, devices and systems for improving hearing and for treating hearing disorders, such as auditory neuropathies. A hearing enhancement system of this invention generally comprises; an amplitude modulation processor, a frequency high-pass processor, a frequency upward-shifting processor and a formant upward-shifting processor.

16 Claims, 4 Drawing Sheets

METHODS, DEVICES AND SYSTEMS USING SIGNAL PROCESSING ALGORITHMS TO IMPROVE SPEECH INTELLIGIBILITY AND LISTENING COMFORT

RELATED APPLICATION

This application claims priority to U.S. Provisional Patent Application No. 60/688,918 filed on Jun. 8, 2005, the entirety of which is expressly incorporated herein by reference.

STATEMENT REGARDING GOVERNMENT SUPPORT

This invention was made with Government support under NIH/NIDCD grant no. RO1-DC-02267-07. The Government has certain rights in this invention.

FIELD OF THE INVENTION

The present invention relates generally to the fields of bioengineering and medicine and more particularly to methods, devices and systems that use signal processing algorithms to improve hearing in hearing impaired subjects.

BACKGROUND OF THE INVENTION

The function of a conventional hearing aid is to amplify acoustic signals to make sounds audible to hearing-impaired individuals. Its basic structure consists of a microphone, an amplifier, a receiver and a power supply. The amplifier is the major component that magnifies the input speech signal. In the past five years, digital signal processing (DSP) has been introduced into hearing aid design. After analog speech signals are converted into digital form by an analog-to-digital converter, the signals can be manipulated by sophisticated processing algorithms before being converted back into the analog domain. Compared to standard analog hearing aids, digital aids provide more and precise controls over a broad range of parameters: the gain, frequency response and compression. Moreover, these settings can be individually programmed in each frequency band. Current digital hearing aids allow much detailed controls over hearing aid functions, but its one and only function is to amplify the signal.

Two types of amplification are used in hearing aid design. The linear amplifier limits the maximum output from peak clipping, which occurs when the electrical signal exceeds the maximum output of some component of the hearing aid circuit or when the digital signal exceeds the maximum digital number a finite number of bits can represent. This limitation causes various forms of distortion that reduces the intelligibility and subjective quality of speech. Current hearing aids use a non-linear amplifier, which reduces the gain as the output or input approach the maximum values. Compression is implemented by an analog circuit or by a digital processing algorithm to reduce the gain of the instrument when either the input or output exceeds a predetermined level. This type of amplification results in a wider dynamic range input to hearing-impaired patients, making soft sounds audible without making loud sounds uncomfortably loud. However, amplitude compression also changes the temporal properties of the original speech signal and may cause side effects in speech intelligibility. We will extend this point in our research.

Conventional hearing aids do not work for all hearing impairments. The primary function of conventional hearing aids is to amplify and make the speech signal audible within the constraints of a person's hearing thresholds and loudness tolerance levels. They solve the problem of hearing loss only when it is the amplification function of the ear that is defective, such as in sensorineural hearing loss due to outer hair cell loss and/or damage. No matter how sophisticated the instrument is, this type of hearing aid cannot solve the problem for other types of hearing loss, such as neural fiber removal in tumor-treated operations, which leave patients with little or no residual hearing, damage in inner hair cells, neuropath or brainstem, which not only affect intensity discrimination but also introduce sound distortion.

Digital signal processing allows for more complicated algorithms that may be used to compensate for these types of hearing loss. The transposer hearing aid is one such example designed to help patients without residual hearing at high frequencies. High frequency speech sounds are transposed and delivered to the low frequency region where patients are likely to have more residual hearing and more likely to be able to use that information. In this transposition process, high-frequency consonants are squeezed and transposed to the low-frequency range with original low-frequency vowels and consonants untouched. Although the original input is distorted and an unnatural sound is produced, more useful information is delivered to the audible frequency range, improving the user's perceptual capacity.

Neither conventional nor transposer hearing aids have achieved much success on patients with auditory neuropathy, a recently discovered hearing disorder that has unique pathologies and perceptual consequences. Auditory neuropathy may involve loss of inner hair cells (IHC), dysfunction of the IHC-nerve synapses, neural demyelination, axonal loss or possible combinations of any of the above. Clinically, these pathologies may be mixed with traditional cochlear impairment involving OHCs and/or central processing disorders involving the brainstem and cortex. Because one possible neural mechanism underlying the AN symptoms is the desynchronized discharge in the auditory nerve fibers, auditory neuropathy has also been termed "auditory dys-synchrony." Auditory neuropathy not only causes sound attenuation, but also sound distortion, which cannot be compensated by either conventional or transposer hearing aids. New processing strategies should be developed to rectify the problem of sound distortion.

Clinical and psychoacoustic testing on auditory neuropathy subjects have been conducted to investigate the root causes of sound distortion. Pure-tone audiograms of auditory neuropathy subjects show a global trend opposite to regular hearing impairment—high thresholds at low frequencies but low or relative normal thresholds at high frequencies—implying that amplifying energy at high frequencies or transposing high-frequency components to the low-frequency range may not help. Test results from the temporal modulation transformation function (TMTF) show that auditory neuropathy patients have poorer temporal modulation discrimination ability than normal-hearing and other hearing-impaired people. It again implies that conventional hearing aids will not work for them since their degraded temporal modulation cannot be compensated. In addition, data from gap detection tests showed lower gap discrimination ability in auditory neuropathy than other hearing impairments, suggesting that auditory neuropathy patients have impaired temporal processing ability, which cannot be compensated by the conventional and transposer hearing aids. New strategies may be developed based on these clinical and psychoacoustic data to solve the problem of sound distortion in auditory neuropathy.

Various strategies have been proposed to help auditory neuropathy patients to hear clearer. One strategy is to increase modulation index in each different frequency band to compensate for the temporal modulation loss due to desynchronized discharges in the auditory nerve fibers in auditory neuropathy. This can be implemented over each extracted envelope in each frequency band and implemented by directly increasing the amplitude of peaks and decreasing the amplitude of troughs in a local temporal range. This method is definitely different from the amplification process used in conventional hearing aids, which amplify both the peaks and troughs. The conventional hearing aids keep the modulation depth the same as the original signal in linear compression, or even decrease the modulation depth in nonlinear compression. The amplitude of peaks cannot be amplified by the same ratio as the amplitude of valleys in nonlinear compression and worsened performance is predicted because of the degraded temporal modulations introduced in conventional hearing aids. The proposed strategy will change the amplitude of peaks and troughs in the opposite direction increase the fluctuations in temporal envelope in each frequency band. Most previous studies testified the importance of the amplitude modulation in speech intelligibility, but enhancement of the modulation has not been used in hearing aid technology and auditory neuropathy, to the best of our knowledge.

Aside from compensating for the temporal amplitude modulation deficit, the new strategies also compensate for hearing loss at low frequencies in auditory neuropathy. One strategy is to filter out all low frequency components based on psychoacoustic observations that auditory neuropathy patients have extremely poor pitch perception at low frequencies but relatively normal pitch processing at high frequencies. The high-pass filter's cutoff frequency is set based on the individual's audiogram. The assumption is that the distorted low frequency processing may confound auditory neuropathy patients' pitch perception at high frequencies. Once the part of signal that causes sound distortion is removed, higher speech recognition performance should be achieved.

Another strategy has been to compensate for the low frequency hearing loss by transposing low frequency components to high frequency range based on the individual's audiogram. We note that this frequency transposition is in the opposite direction as implemented in current transposing hearing aids, which typically transpose high-frequency signals to the low-frequency region to solve the lack-of-audibility problem at high frequencies. Both frequency components in low frequency range, in which no signal is audible even after being maximally amplified, and frequency components in the audible higher frequency range will be linearly or nonlinearly shifted to the higher frequency range. This processing shifts all frequency components, including the original audible high frequency components, which may make the processed sound have unnatural voice quality.

SUMMARY OF THE INVENTION

The present invention provides methods, devices and systems which improve the naturalness of processed sound by separating the information-bearing spectral envelope from the voice-quality-bearing spectral fine structure. The spectral envelope (formants) are estimated in real time and shifted to a higher frequency range, whereas the fine structure is kept intact. These methods, devices and systems of the present invention provide benefits such as greater than linear and nonlinear frequency shifting. However, more complicated calculations are required in digital signal processing. The temporal modulation strategy, which compensate for the temporal processing deficit, can be used in combination with any one of the three strategies that compensate for the hearing loss and distortion at low frequencies. In some embodiments of this invention, the low frequency components are processed before changing the temporal modulation thereby preventing the temporal modulation from being compromised in the subsequent processing step.

In accordance with the present invention, there is provided a hearing enhancement system which comprises (a) an amplitude modulation processor, (b) a frequency high-pass processor, (c) a frequency upward-shifting processor and (d) a formant upward-shifting processor. The amplitude modulation processor is operative to enhance temporal modulation and/or to improve speech intelligibility. The frequency high-pass processor, frequency upward-shifting processor and formant upward-shifting processor are operative to compensate for low frequency hearing loss.

Further in accordance with the present invention, there is provided a system of the foregoing character wherein the amplitude modulation processor is operative to increase amplitude modulation in different frequency bands based on subjects' temporal modulation transfer function (TMTF).

Still further in accordance with the present invention, there is provided a system of the foregoing character wherein the frequency high-pass processor is operative to remove low frequency components that can adversely affect a patient's pitch perception at low frequencies.

Still further in accordance with the present invention, there is provided a system of the foregoing character wherein the frequency upward-shifting processor is operative to cause linear or non-linear transposition of low frequencies to more audible high frequencies.

Still further in accordance with the present invention, there is provided a system of the foregoing character wherein the upward-shifting processor is operative to increase formant frequencies without significantly changing voice quality.

Still further in accordance with the present invention, there is provided a system of the foregoing character wherein the modulation processor is operative to improve the clarity of a speech signal or other signal transmitted over a wired or wireless transmission channel.

Still further in accordance with the present invention, there is provided a system of the foregoing character wherein the system comprises or is incorporated into a hearing aid, cochlear implant, intraneural electrode implant or other device that is carried, worn or implanted in the body of a human or animal subject for the purpose of improving hearing or sound recognition.

Still further in accordance with the present invention, there is provided a method for improving hearing and/or sound (e.g., speech) recognition in a human or animal subject by implanting, inserting, attaching, affixing or associating with the subject's body a system of the foregoing character.

DETAILED DESCRIPTION AND EXAMPLES

Figure 1:
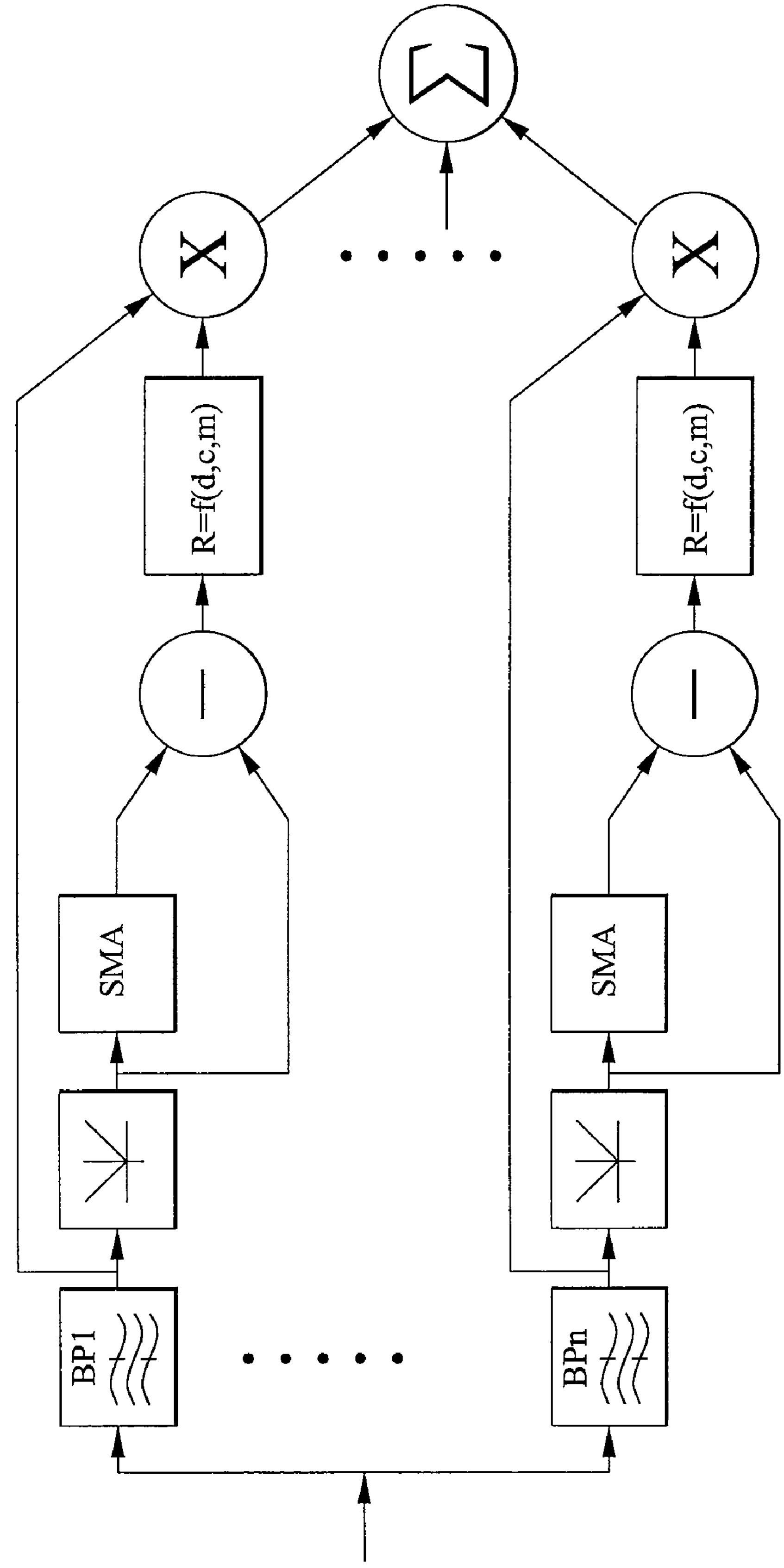
FIG. 1 is a block diagram of an amplitude modulation processor of the present invention.

The following detailed description and the accompanying drawings are intended to describe some, but not necessarily all, examples or embodiments of the invention. The contents of this detailed description and the accompanying drawings do not limit the scope of the invention in any way.

The present invention provides new signal processing strategies (e.g., methods), devices and systems useable to improve speech intelligibility and listening comfort, in quiet and/or noisy environments, for normal-hearing or hearing-impaired people. The new signal processing strategies (e.g., methods) of the present invention may be used to program and/or operate devices, such as processors employed in hearing aids, cochlear implants and other hearing enhancement devices and systems.

In accordance with the invention there are provided hearing enhancement systems that comprise four processors, namely, 1) an amplitude modulation processor, 2) a frequency high-pass processor, 3) a frequency upward-shifting processor and 4) a formant upward-shifting processor. The amplitude modulation processor may be used to enhance temporal modulation and to improve speech intelligibility. The frequency high-pass processor, frequency upward-shifting processor and formant upward-shifting processor may be used to compensate for low frequency hearing loss as typically occurs in patients who suffer from auditory neuropathy.

The amplitude modulation processor may be designed to increase amplitude modulation in different frequency bands based on subjects' temporal modulation transfer function (TMTF). The frequency high-pass processor is designed to remove low frequency components that might confound patients' pitch perception at low frequencies. The frequency upward-shifting processor linearly or non linearly transposes the low frequencies which are hardly audible for some hearing impaired listeners to an audible high frequency range. The formant upward-shifting processor increases the formant frequencies without changing significantly the voice quality.

These strategies are aimed to improve speech perception for normal hearing and hearing impaired listeners, especially for auditory neuropathy patients. Furthermore, the modulation processor can be used to improve the clarity of the transmitted speech signal over wired or wireless transmission channels.

Current conventional hearing aids do not provide any of the proposed functions and provide mostly amplification. The proposed algorithms may or may not amplify the sound, rather they accentuate critical features for speech intelligibility and listening comfort. In the cases of auditory neuropathy, the problem is not only sound attenuation, but rather sound distortion due to neural hearing loss. Clinical and psychophysics testing shows auditory neuropathy patients have poor pitch perception at low frequencies and impaired temporal processing ability. New strategies have been developed based on these clinical and psychophysics data to solve the problem of sound distortion in auditory neuropathy.

FIG. 1 shows an analysis-by-synthesis block diagram of a modulation processor of the present invention. The original sound signal is divided into a plurality of N sub-bands for using a filter bank equally distributed on a logarithmic scale. The signal in each frequency band was full-wave rectified first, and then passed through a simple moving average (SMA) filter to produce a slowly varied or smoothed signal. A point-by-point difference (d) was calculated between the rectified waveform and its smoothed version, which served as an input to the amplitude modulation modification function (R). The modulation modification function also took into account the constant maximal value (m) and the expected modulation compensation (c) and calculated the ratio to determine how much the original signal needed to be amplified or compressed on a real-time basis. Finally, the synthesizer summed the modified signals from all subbands to produce a new signal that contained enhanced amplitude modulations.

Figure 2:
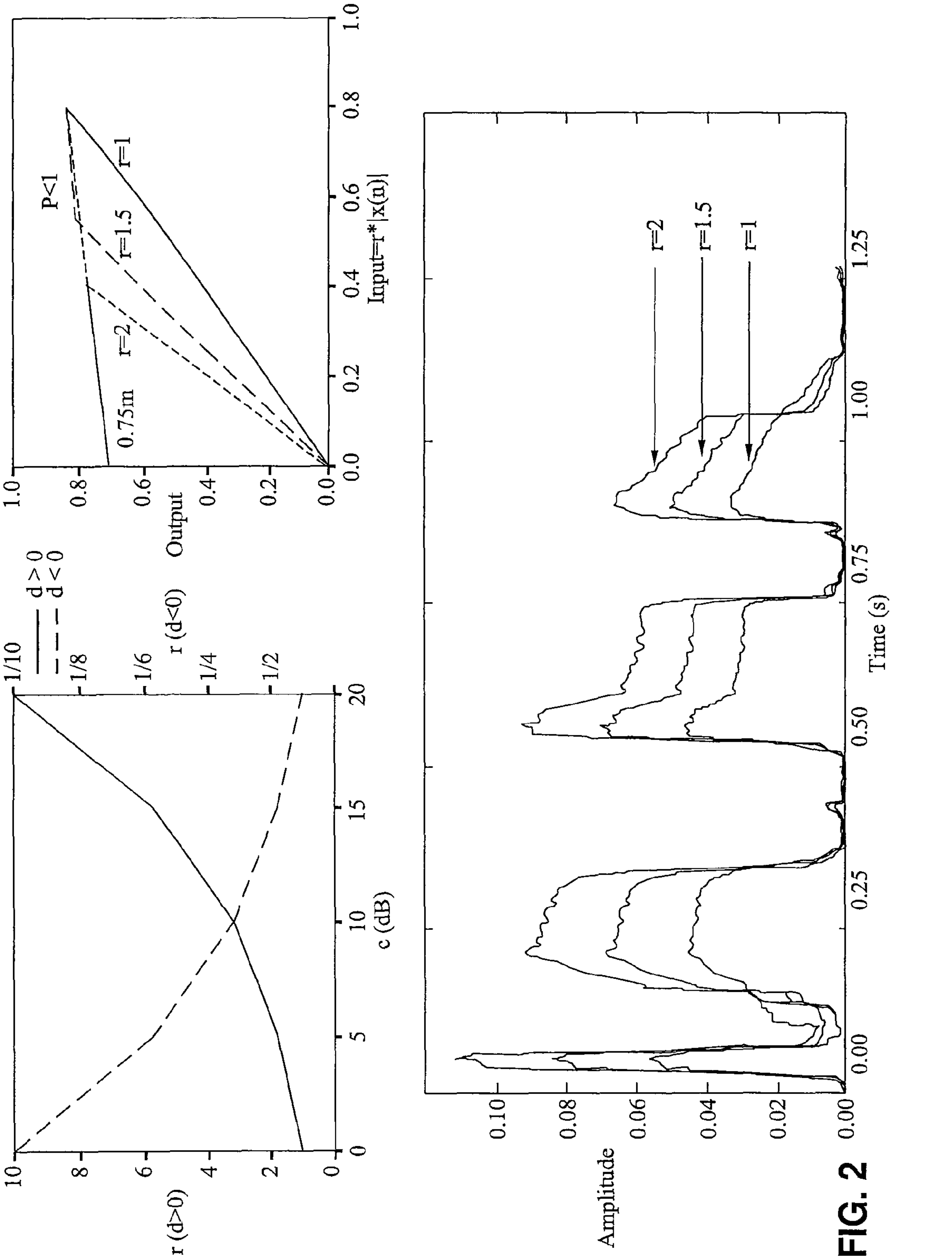
FIG. 2 consists of graphs showing details of the modulation modification function of the modulation processor of FIG. 1. The upper left panel shows scale ratio (r) as the function of threshold difference (c) and the aforementioned waveform difference (d). The upper right panel shows amplitude output as a function of the input scaled by the scale ratio r. The bottom panel shows an example of the original envelope (r=1) and the processed envelops with r equal to 1.5 and 2.

The upper left panel in FIG. 2 shows the scale ratio (r) as a function of the threshold difference (c) and the calculated point-by-point difference (d). A positive or negative d value corresponds to the arrival of a peak or trough and would be expanded or compressed by a ratio greater or less than 1 to increase modulation. The output of the function was actually the linear mapping of the input dB values when d was greater than 1 and the reciprocal of the linear mapping when d was less than 1. For example, a 6-dB modulation compensation (c) with a positive d will result in a scale value of 2 to expand the peak, but a negative d will result in a value of ½ to compress the trough. The second stage compressed the signal to prevent the output from clipping at peaks. The upper right panel in FIG. 2 shows the amplitude output as a function of the input scaled by the scale ratio r from the first stage. A family of curves with different scale ratios showed different compressing functions for r=1, 1.5 and 2.0. 75% of the maximal value (m) was set to the knee point for all functions. If the amplitude of the scaled input is greater than the knee point amplitude, the output will be compressed by a value calculated from Equation 1 to prevent from saturation, otherwise the compressor will be bypassed. In Equation 1, G is the compressed gain, x(n) is the input and p is the compression factor, which was set to ¼ and whose typically practical values are ¼ to ½. The bottom panel in FIG. 2 shows the envelope with scale values of 1.5 and 2 had higher peaks and lower troughs than the unprocessed envelope (r=1).

$$G(x(n))=(r\times x(n)/0.75\times m)^{p-1} \tag{1}$$

Figure 3:
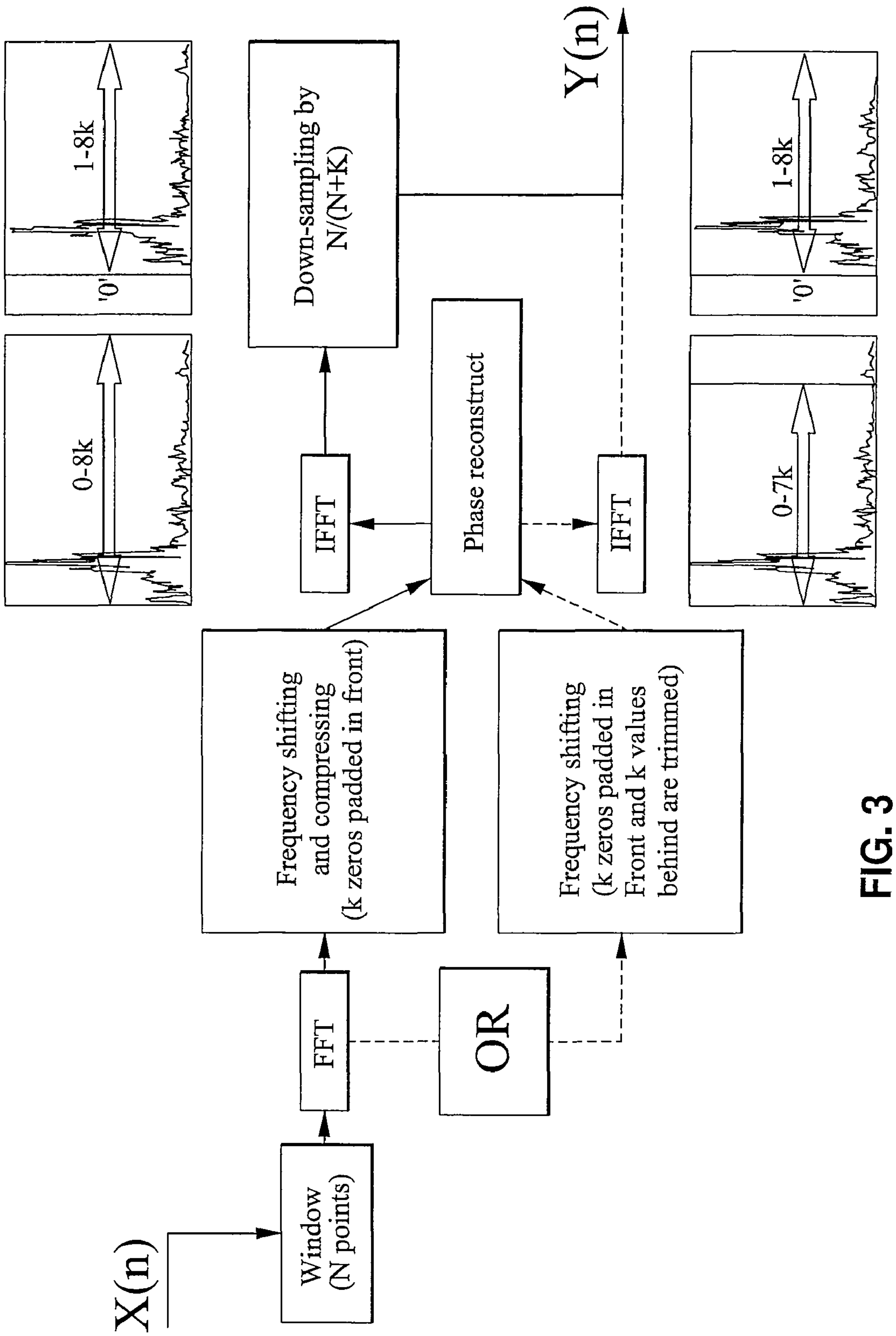
FIG. 3 is a block diagram for a frequency upward-shifting processor.

FIG. 3 shows an example of the digital implementation of a frequency upward-shifting processor in accordance with the present invention. The digital waveform, X (n), was converted into a digital signal in the frequency domain by means of an FFT (Fast Fourier Transform) program. A linear or nonlinear frequency shifting can then be implemented. The linear shifting implementation may be similar to the analog implementation in terms of functionality, i.e., simply shifting all frequency components by the same amount in frequency that was determined by the "knee point" frequency on the audiogram. In present implementation, this knee point is usually 1 to 2 kHz, instead of 12 kHz as implemented in previous analog transposer implementations. Because the shifted frequency Δω introduced a change of phase difference in each frequency bin between the current and the successive frame in the windowed FFT analysis, reconstructing phase was necessary. The phase values had to be reconstructed to match Δω in shifted frequency bins. This can be accomplished by multiplying frequency bins by the complex value $Z_u$ in Equation 3. R was the hop size and calculated by multiplying the window size N and overlapping factor K (see Equation 4). For example, a 50% overlap will result in a hop size of N/2. Depending the knee-point frequency, zeros were padded in the beginning of the FFT array while the extra high-frequency components were simply trimmed. The number of zeros was determined by the knee-point frequency (Fk), the sampling frequency (Fs) and the number of FFT (N) in Equation 2:

$$\text{Number\_of\_Zeros}=2NF_k/F_s \quad (2)$$

$$Z_u=e^{j\Delta\omega R} \quad (3)$$

$$R=N\times K \quad (4)$$

Unlike the linear shifting in which of the extra high-frequency components were trimmed, the nonlinear upward shifting preserved all frequency components by compressing the whole frequency range into a narrower range between the knee-point frequency and the original high-frequency boundary. In the case of 1-kHz knee-point, the original 0-8 kHz range was compressed into a 1-8 kHz range. In actual implementation, the magnitude and phase were processed separately because the mapping processing could deal with real values only. For the magnitude, the re-sampling method was used to calculate the mapped values. To nonlinearly shift the frequency components from 0-8 kHz to 1-8 kHz, the original magnitude values for 0-8 kHz were first linearly shifted to 1-9 kHz and then were down-sampled to a 7-kHz range with the ratio of 8 to 7. The phase values had to be reconstructed to match the shifted frequency Δω in each frequency bin as described earlier. The mapped complex values were obtained by multiplying the modified magnitudes and the sinusoid of the reconstructed phase from the real part and the cosine of that from the imaginary part. An inversed FFT was implemented to re-synthesize the signal.

Figure 4:
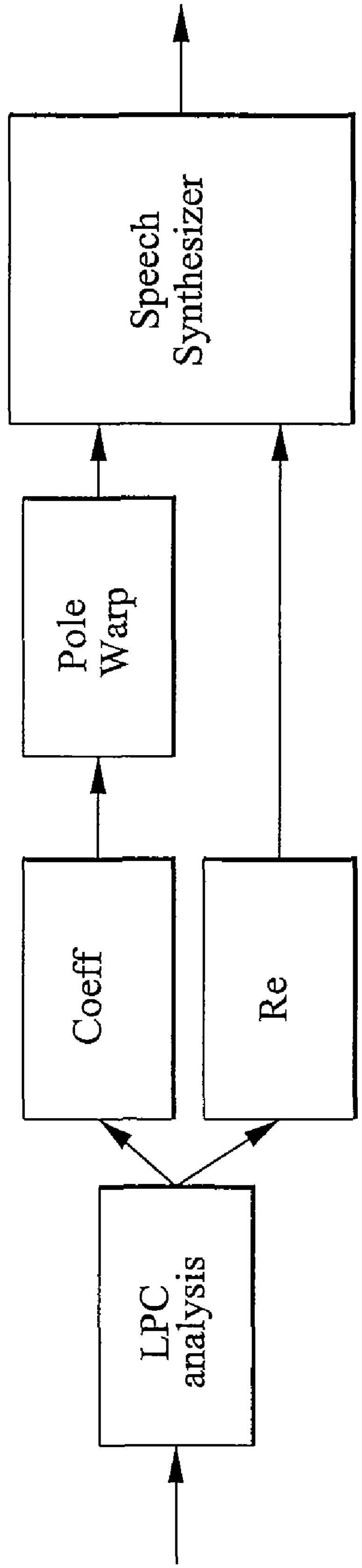
FIG. 4 is a block diagram for a formant upward-shifting processor.

FIG. 4 shows an example of a formant upward-shifting implementation diagram in accordance with the present invention. In this example, the input speech was passed through a $14^{th}$-order linear prediction coding (LPC) analyzer, which extracted 14 coefficients that determines formant frequencies while the residue from the errors in the linear prediction coding serving as the excitation source for the synthesizer. The LPC coefficients were warped to shift the formants while the residue was kept intact, resulting in synthesized with shifted formants but intact harmonic structure.

The proposed strategies can be used to provide improved speech recognition and listening comfort for both normal-hearing and hearing-impaired listeners, particularly those with auditory neuropathy. The corresponding DSP code can be integrated into the regular hearing aid for auditory neuropathy patients to improve speech perception. In addition, the converted clear speech can be used in difficult hearing environments to make the speech clear.

It is to be appreciated that the invention has been described herein with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A hearing enhancement system comprising:

an amplitude modulation processor;

a frequency high-pass processor;

a frequency upward-shifting processor; and a formant upward-shifting processor.

2. A system according to claim 1 wherein the amplitude modulation processor is operative to enhance temporal modulation and/or to improve speech intelligibility.

3. A system according to claim 1 wherein the frequency high-pass processor, frequency upward-shifting processor and formant upward-shifting processor are operative to compensate for low frequency hearing loss.

4. A system according to claim 1 wherein the amplitude modulation processor is operative to increase amplitude modulation in different frequency bands based on subjects' temporal modulation transfer function (TMTF).

5. A system according to claim 1 wherein the frequency high-pass processor is operative to remove low frequency components that can adversely affect a patient's pitch perception at low frequencies.

6. A system according to claim 1 wherein the frequency upward-shifting processor is operative to cause linear or non-linear transposition of low frequencies to more audible high frequencies.

7. A system according to claim 1 wherein the upward-shifting processor is operative to increase formant frequencies without significantly changing voice quality.

8. A system according to claim 1 wherein the modulation processor is operative to improve the clarity of a speech signal or other signal transmitted over a wired or wireless transmission channel.

9. A system according to claim 1 wherein the amplitude modulation processor is operative to (a) divide sound into a plurality of N sub-bands, (b) full-wave rectifying the sub-bands and then passing the rectified waveform through a simple moving average (SMA) filter to produce a smoothed signal, (c) calculating a point-by-point difference between the rectified waveform and its smoothed signal and (d) inputting the calculated point-by-point difference into an amplitude modulation modification function.

10. A system according to claim 9 wherein the modulation modification function takes into account a constant maximal value (m) and an expected modulation compensation (c) and calculates the ratio of those values to determine how much real time amplification or compression of the original signal is needed.

11. A system according to claim 1 wherein the frequency upward-shifting processor converts a digital waveform, X (n), into a digital signal in the frequency domain by means of a Fast Fourier Transform program.

12. A system according to any preceding claim wherein the format upward-shifting processor performs a nonlinear upward shifting whereby the frequency range is compressed into a narrower range between a knee-point frequency and an original high-frequency boundary.

13. A system according to any preceding claim wherein the system comprises or is incorporated into a hearing aid.

14. A system according to any preceding claim wherein the system comprises or is incorporated into a cochlear implant.

15. A method for improving hearing and/or speech recognition in a human or animal subject, said method comprising the step of implanting, inserting, attaching, affixing or associating with the subject's body as hearing enhancement system according to claim 1.

16. A method according to claim 15 wherein the method is carried out to treat hearing impairment resulting from auditory neuropathy.

* * * * *